(12) United States Patent
Roche Rebollo et al.

(10) Patent No.: US 11,701,143 B2
(45) Date of Patent: *Jul. 18, 2023

(54) CATHETER DEVICES, NEEDLE ASSEMBLIES, KITS AND METHODS

(71) Applicant: VASCULAR BARCELONA DEVICES, S.L., Barcelona (ES)

(72) Inventors: Enrique Roche Rebollo, Barcelona (ES); Guiu Llusa Melendez, Barcelona (ES)

(73) Assignee: VASCULAR BARCELONA DEVICES, S.L., Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 17/752,280

(22) Filed: May 24, 2022

(65) Prior Publication Data

US 2022/0280185 A1 Sep. 8, 2022

Related U.S. Application Data

(63) Continuation of application No. 16/264,953, filed on Feb. 1, 2019, now Pat. No. 11,357,539, which is a
(Continued)

(30) Foreign Application Priority Data

Aug. 3, 2016 (EP) .................... 16382384

(51) Int. Cl.
A61B 17/34 (2006.01)
A61B 17/3209 (2006.01)
(Continued)

(52) U.S. Cl.
CPC .... *A61B 17/3415* (2013.01); *A61B 17/32093* (2013.01); *A61M 25/0606* (2013.01);
(Continued)

(58) Field of Classification Search
CPC ........ A61M 25/0606; A61M 25/09041; A61M 2025/0096; A61M 2209/06;
(Continued)

(56) References Cited

U.S. PATENT DOCUMENTS 4,629,450 A 12/1986 Suzuki et al.
4,929,246 A 5/1990 Sinofsky
(Continued)

FOREIGN PATENT DOCUMENTS

CN 102824666 A 12/2012
DE 10100332 A1 7/2002
(Continued)

OTHER PUBLICATIONS

International Search Report and Written Opinion, PCT/EP2014/079311, dated May 15, 2015.
(Continued)

*Primary Examiner* — Kevin C Sirmons
*Assistant Examiner* — Avery Smale
(74) *Attorney, Agent, or Firm* — Edell, Shapiro & Finnan, LLC

(57) ABSTRACT

Examples of catheter devices, removable needle devices and kits are disclosed. Also methods for accessing a hollow organ are disclosed. The catheter devices include a body extending longitudinally from a proximal end to a distal end, wherein the body includes an elongated channel along a longitudinal length of the body extending from the proximal end to the distal end of the body, wherein the elongated channel is configured to receive an elongated needle of the removable needle device, and the body includes one or more cutting edges extending in a proximal direction from the distal end of the body. The body of the catheter devices includes one or more recesses adapted to mate with one or more catches of the removable needle device for coupling
(Continued)

the needle device to the catheter device. Methods of using the catheters, removable needle devices and the kits are also disclosed.

20 Claims, 10 Drawing Sheets

Related U.S. Application Data continuation of application No. PCT/EP2017/069323, filed on Jul. 31, 2017.

(51) Int. Cl.
*A61M 25/06* (2006.01)
*A61M 25/09* (2006.01)
*A61M 25/00* (2006.01)
*A61B 17/32* (2006.01)

(52) U.S. Cl.
CPC .......... *A61M 25/09041* (2013.01); *A61B 2017/320052* (2013.01); *A61B 2017/3454* (2013.01); *A61M 25/0097* (2013.01); *A61M 25/0662* (2013.01); *A61M 2209/06* (2013.01)

(58) Field of Classification Search
CPC .. A61M 25/0097; A61M 25/01; A61M 25/02; A61M 2025/024; A61M 25/0612; A61M 25/0637; A61M 2025/0004; A61M 2025/0006; A61M 2025/0175; A61M 25/09; A61B 17/3415; A61B 17/32093; A61B 2017/320052; A61B 17/32; A61B 2017/320044; A61B 2017/3454; A61B 2017/320074; A61B 2017/320075; A61B 2017/320082
See application file for complete search history.

(56) References Cited

U.S. PATENT DOCUMENTS

| | | | |
|---|---|---|---|
| 4,955,890 | A | 9/1990 | Yamamoto et al. |
| 5,317,938 | A | 6/1994 | de Juan, Jr. |
| 5,693,030 | A | 12/1997 | Lee et al. |
| 6,077,284 | A | 6/2000 | Piraka |
| 6,379,332 | B1 | 4/2002 | Van Landuyt |
| 9,743,952 | B2 * | 8/2017 | Kiev ................ A61B 17/32093 |
| 2002/0040231 | A1 | 4/2002 | Wysoki |
| 2004/0030319 | A1 | 2/2004 | Korkor et al. |
| 2007/0060889 | A1 * | 3/2007 | Adams ............... A61B 17/3415 |
| | | | 604/164.01 |
| 2008/0262430 | A1 * | 10/2008 | Anderson ............. A61M 25/09 |
| | | | 604/165.01 |
| 2009/0254038 | A1 | 10/2009 | Lapeyre |
| 2011/0137395 | A1 | 6/2011 | Fargahi |
| 2013/0178711 | A1 | 7/2013 | Avneri et al. |

FOREIGN PATENT DOCUMENTS

| | | |
|---|---|---|
| ES | 2575861 T3 | 7/2016 |
| GB | 904237 A | 8/1962 |
| WO | 0110345 A1 | 2/2001 |
| WO | 2007035889 A2 | 3/2007 |
| WO | 2014027268 A1 | 2/2014 |
| WO | 2016015787 A1 | 2/2016 |

OTHER PUBLICATIONS

International Search Report and Written Opinion, PCT/2017/069323, dated Jan. 4, 2018, 11 pages.

* cited by examiner

CATHETER DEVICES, NEEDLE ASSEMBLIES, KITS AND METHODS

CROSS-REFERENCE TO RELATED APPLICATIONS

This application is a continuation of U.S. application Ser. No. 16/264,953, filed Feb. 1, 2019, which relates to and claims the benefit and priority to International Application No. PCT/EP2017/069323, filed Jul. 31, 2017, which relates to and claims the benefit and priority to European Patent Application No. EP16382384.2, filed Aug. 3, 2016.

FIELD

The present disclosure relates to catheter devices configured to provide access to hollow organs. The present disclosure further relates to kits including such catheter devices and methods for using catheter devices, in particular for accessing hollow organs. Hollow organs, as used herein explicitly include bodily lumens, e.g. cavities and tubular organs.

BACKGROUND

Medical procedures to obtain access through a patient's skin to hollow organs such as e.g. blood vessels are widely used and for many different kinds of interventions, e.g. endovascular repair, angioplasty, insertion of chest drains etc.

One known technique used in such procedures is the Seldinger technique which can be used e.g. for vascular access, or for placement of pleural, peritoneal, cardiac, and enteral drains and tubes. This procedure usually involves the following steps depicted in FIG. 1: A puncture is performed with an introducer needle (or "trocar") 20 placed through the patient's skin and into the hollow organ 21 of concern (step A). A soft-tipped guide wire 22 is then passed through the lumen of the introducer needle 20 and brought into a desired position within the hollow organ 21 (step B). Then, the needle 20 is withdrawn while the guide wire 22 remains in the hollow organ 21 (step C). At this point of the procedure, a guide catheter 23 e.g. a blunt cannula or other devices which allows investigation or treatment of the hollow organ may be passed over the guide wire (step D). Once the guide catheter 23 is placed in the correct position for investigation or treatment of the hollow organ, the wire is removed (step E).

The guide catheters by necessity are larger than the guide wire over which they are passed and hence cannot pass through the skin via the small hole made by the initial needle puncture, thus an enlargement of the puncture site may be needed. For this reason, a small skin incision is made adjacent to the puncture site i.e. the point of entry of the guide wire into the skin. This enlargement of the puncture site may be made with a sharp instrument e.g. a surgical scalpel. However, this requires great dexterity and it is difficult to make a precise incision. Accidents can occur if the incision is made too deep or too long in case the surgeon does not have a good enough control. This may lead to hemorrhage or perforation of the hollow organ (e.g. vein). In addition, creating and enlarging the puncture site may be time consuming, which increases stress for the patient. There is also the risk of cutting the guide wire, which is a very thin wire. And it also happens that a cut is made which is not exactly at the puncture site. Moreover the procedure supposes a risk for accidental injury for the practitioner.

WO2016015787 discloses a catheter device configured to provide access to a hollow organ. It includes a body extending longitudinally from a proximal end to a distal end and a flexible insertion tube extending longitudinally from a proximal end to a distal end, wherein the body comprises: an elongated channel along the longitudinal length of the body extending from the proximal end of the body to the distal end of the body, wherein the channel is configured to receive an elongate needle. The body further comprises one or more cutting edges extending rearwardly from a distal end of the body. Furthermore, the flexible insertion tube of the catheter device is coupled to the distal end of the body and comprises a tubular elongated passage aligned with the tubular elongated channel of the body forming a lumen.

WO2007035889 describes an introducer apparatus with a plurality of cutting edges along the outer surface of the distal end of an introducer with a blunt distal end. The introducer may be adapted to extend from and be withdrawn into the sheath. The cutting edges may resect tissue located around the insertion site.

It is an object of the present disclosure to provide improved catheter devices, needle assemblies, (surgical) kits, and methods that at least partially resolve some of the aforementioned problems.

SUMMARY

In a first aspect, a catheter device configured to provide access to a hollow organ is provided. The catheter device comprises a catheter body extending longitudinally from a proximal end to a distal end, wherein the catheter body comprises an elongated channel along the longitudinal length of the catheter body extending from the proximal end to the distal end of the catheter body, wherein the channel is configured to receive an elongated needle of a removable needle device. The catheter body further comprises one or more cutting edges extending in a proximal direction from a distal end of the body, and one or more recesses adapted to mate with one or more catches of the needle assembly for coupling the needle device to the catheter device.

Distal herein is to be understood as a side of an instrument further away from a person (e.g. nurse or doctor) using it. Proximal herein is to be understood as the opposite side.

According to this first aspect, a catheter device that is configured to provide a double function of providing access to a hollow organ and to facilitate the introduction of larger devices is provided. To this end, the catheter device is provided with one or more cutting edges. These cutting edges may enlarge a puncture or a nick previously made in the patient's skin. Hereby the use of supplementary cutting instruments such as scalpels may be avoided. With this arrangement, the risk of accidents that can occur when manipulating the cutting instrument e.g. cutting off the guide wire and/or making the nick too deep or too long are also avoided. In addition, the risk of making by mistake a second puncture near the first puncture instead of enlarging the first puncture is also avoided since the incision is made larger by simply guiding the catheter along the guide wire.

In some examples, the needle may be a hollow needle. In some examples, the catheter body may comprise an insertion tube arranged at a distal end of the catheter body, and the lumen of the insertion tube is aligned with the elongate channel in the catheter body.

The procedure for accessing e.g. a vein through the patient's skin is inherently improved. The catheter with cutting edges as proposed herein may be held and used in the same way as traditional trocars or Abbocaths ("hollow needle within a tube", typically made of Teflon). In a very similar manner as in the traditional method, the initial puncture may be made.

In examples wherein a catheter device including an insertion tube is used, the needle can then be immediately removed. A guide wire may be introduced into the organ (vein) through the channel in the catheter that previously surrounded the needle. Once in place, the catheter body just needs to be advanced a bit along the guide wire in order to increase an incision in a very controlled manner. Since the needle stays in place less time, the risk of an accidental movement by a nurse or other healthcare professional potentially cutting skin or another organ is reduced.

In examples wherein the catheter body does not have an insertion tube and the needle is a hollow needle, the needle may be kept in place while inserting the guide wire. After introduction of the guide wire, the needle can be removed. And similarly as before, the catheter body is advanced over the guide wire to increase the original puncture of the skin.

The catheter may have a variety of shapes. In some examples, the catheter is substantially flat. The cutting edges may extend rearwardly from a distal end of the catheter device and may be substantially straight edges. In other examples, the cutting edges may be curved outwardly. Straight edges provide a constant ratio between axial advancement (of the catheter device) and size of the incision. Edges that are curved outwardly may be more smoothly introduced at the beginning of an incision.

In a further example, a conical cutting edge may be provided. The diameter of the cone may increase from a distal end of the catheter device towards the rear, i.e. towards the proximal end.

In some examples, the one or more cutting edges may comprise consecutive symmetric marks provided at the cutting edges configured to indicate the length of the access into the skin of a patient.

In some examples, the body of the catheter device may be made from a polymer, in particular a polymer that can be sterilized. In preferred examples, the cutting edges and body are integrally formed and made from a suitable polymer. By making the cutting edge from a polymer instead of from more traditional metallic blades, less danger for personnel using the catheter occurs. A catheter could be safely held and no unintentional injury would normally occur.

In some examples, the catheter body may comprise a top surface and a bottom surface, and both the top surface and the bottom surface comprise a recess at or near a proximal end of the body.

In another aspect, a needle device having a handle and a needle is provided. The handle comprises a central portion incorporating a lower pivot and an upper pivot, and further comprising an upper grip arranged to pivot around the upper pivot, and a lower grip arranged to pivot around the lower pivot. The upper grip and lower grip each comprising a catch suitable for mating with a recess in a catheter device, and the needle comprises cutting portion at a distal end of the needle. The central portion of the handle comprises a handle lumen.

The needle device according to this aspect, allows for easy coupling and uncoupling from the catheter device previously described. After puncturing of the skin and reaching the hollow organ, the assembly can be easily disassembled and the needle can be removed easily, before advancing the catheter body towards the skin.

In some examples, the upper pivot and the lower pivot may be spring biased. In particular, the upper and lower pivot may be biased towards a position in which the catches of the grips reach into the recesses of the catheter body.

In a further aspect, a kit is provided including a catheter device any of the examples disclosed herein and a needle device according to any of the examples disclosed herein.

In yet a further aspect, a method for accessing a hollow organ is provided. A catheter device according to any of the examples described herein coupled with a needle device according to any of the examples described herein is provided, such that the needle of the needle device is positioned in the elongate channel of the catheter body. The method comprises making a puncture in a skin of a patient and the hollow organ using the cutting portion of the needle while in the elongate channel of the catheter device. At least a distal part of the needle is introduced into the hollow organ. Then a guide wire is inserted into the elongate channel of the catheter body lumen such that the guide wire is at least partially positioned in the hollow organ. The needle assembly is uncoupled from the catheter device and the needle is removed from the hollow organ. The length of the puncture is increased by inserting the cutting edges of the body of the catheter device into the nick.

In some examples, the needle may be hollow, and the guide wire is inserted while the needle is still in the hollow organ. In other examples, the catheter device comprises an insertion tube and the guide wire is inserted after removing the needle from the hollow organ.

The methods may further comprise removing the catheter device over the guide wire after increasing the length of the puncture and passing a treatment catheter over the guide wire. Optionally, the methods may comprise removing the guide wire.

BRIEF DESCRIPTION OF THE DRAWINGS

Non-limiting examples of the present disclosure will be described in the following, with reference to the appended drawings, in which.

DETAILED DESCRIPTION

Figure 1:
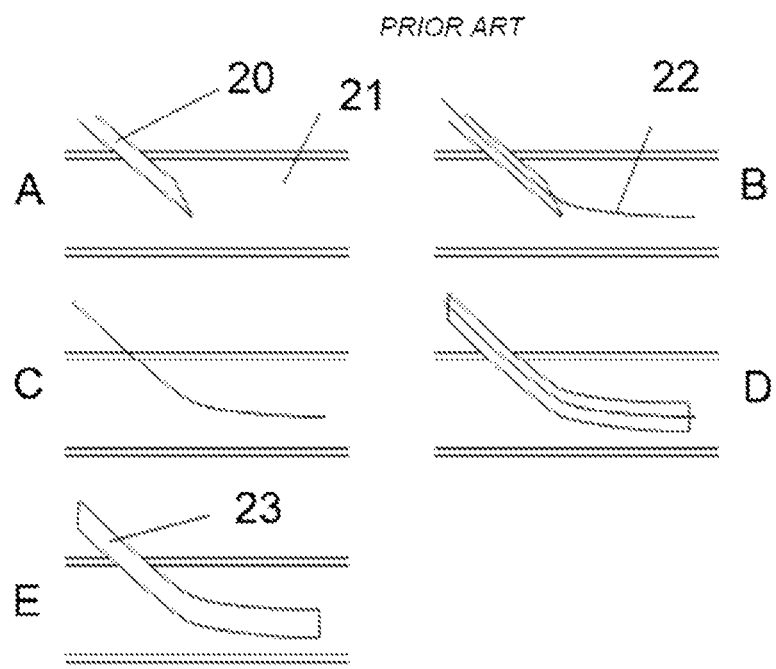
FIG. 1 schematically illustrates a sequence of situations that may occur during the performance of the prior art Seldinger technique.

FIG. 1 shows a prior art technique for accessing a hollow organ which has hereinbefore already been discussed.

Figure 2A:
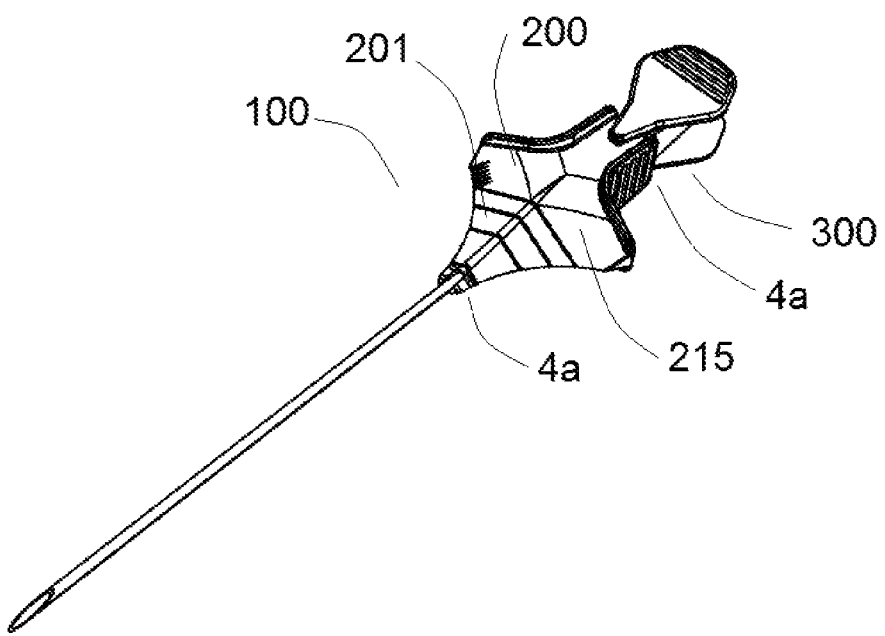
FIGS. 2a-2c schematically illustrate a needle device coupled with a catheter device according to an example.

FIG. 2a schematically illustrates an isometric view of an assembly 100 comprising a catheter device 200, and a needle device 300. The catheter device 200 comprises a catheter body 215. The catheter body 215 has a top surface 201 and a bottom surface 202 (as can be seen in more detail in FIG. 2c). It will be clear that the denomination of top and bottom is arbitrary, as the device can held upside down while retaining the exact same functionality.

The catheter body 215 may extend longitudinally from a proximal end 4a (closer to the person handling the catheter) to a distal end 4b (the end further away from the person handling the catheter).

The body 215 may be made of any plastic suitable for any health product e.g. a PVC plastic, a cured epoxy resin, or some other suitable polymer. Such a polymer could be fibre-reinforced in some examples. In some examples, the distal end 4b of the body 215 may be relatively sharp, thus the insertion of the body 215 into the patient's skin and a hollow organ of the patient may be facilitated.

Figure 2B:
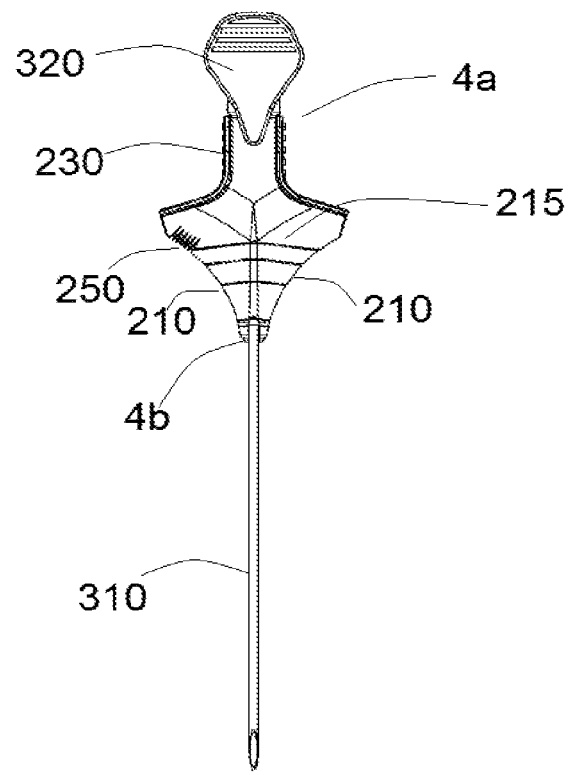
Figure 2C:
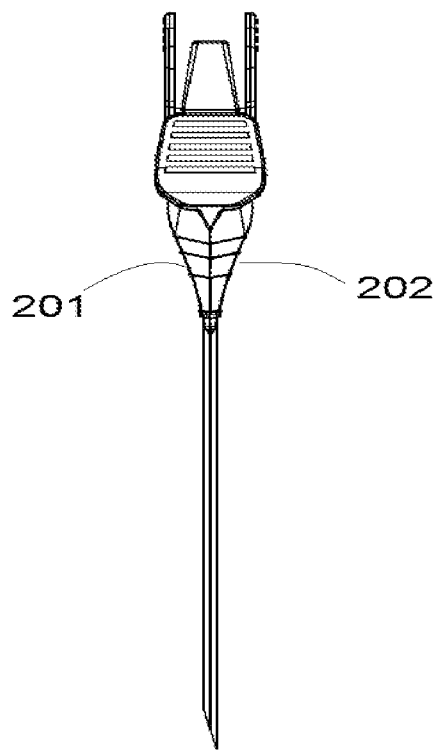

FIG. 2b schematically illustrates a top view of the catheter device shown in FIG. 2a. The catheter body 215 comprises cutting portions 210 which in this example are shown to be curved. The cutting portions 210 in this example are formed by the front edges of the catheter body. In some examples (not illustrated), the cutting portions 210 may be substantially straight, thus a homogeneous control regarding the speed and the length of the enlargement of the nick previously made may be achieved.

Also in both examples so far, the catheter devices can be substantially arrow shaped, but alternative shapes are possible while providing one or more suitable cutting edges or portions.

The catheter body may further comprise a grip 230, which may have a roughness or textured surface for gripping. The grip 230 is shown in this example to be located at or near the proximal end of the body 4a, thus the insertion, removal and manipulation of the body 215 (and thus the whole catheter) may be improved. The grip 230 may generally be shaped so that it may be easily held between the fingers of the user/surgeon. The grip may be shaped as a prism with a substantially rectangular or square cross-section.

The grip 230 may be made of any suitable rough material e.g. plastic polymer, thus the manipulation of the catheter by the user/surgeon may be improved, especially if the grip portion 230 of the catheter is wet, or has saline or body fluids on it. The grip 230 could further have a variety of coatings, including e.g. a hydrophilic coating. With this arrangement, the catheter device may be easily manipulated and used with great accuracy.

As previously commented, the body 215 may comprise one or more cutting edges 210 extending rearwardly from a distal end of the body 4. In this particular example, a first cutting edge 210 and a second cutting edge 210 are shown. The cutting edges 210 may be configured to enlarge a nick previously made on the patient's skin using e.g. a needle device. A saw shaped portion 250 may also be provided (as will be explained with more detail in FIGS. 4a-4c).

Figure 3A:
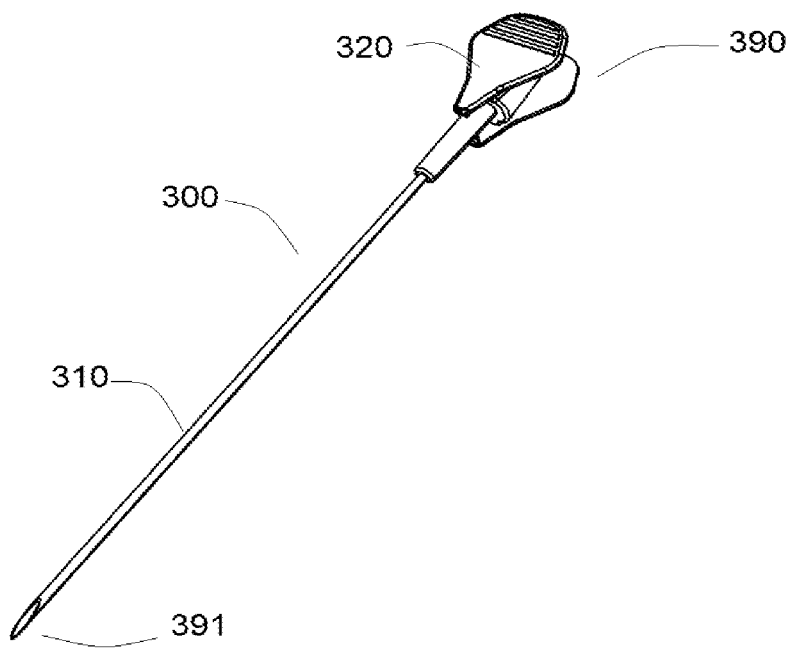
FIGS. 3a-3c schematically illustrate the needle device shown in FIGS. 2a-2c.

The needle device 300 comprises a needle 310 and a handle 320. The needle device 300 is shown in more detail in FIGS. 3a-3c.

The needle device 300 may extend longitudinally from a proximal end 390 (closer to the person handling the catheter) to a distal end 391 (the end further away from the person handling the catheter). The needle device 300 may thus be inserted or withdrawn along a channel defined in the body of the catheter.

Figure 3B:
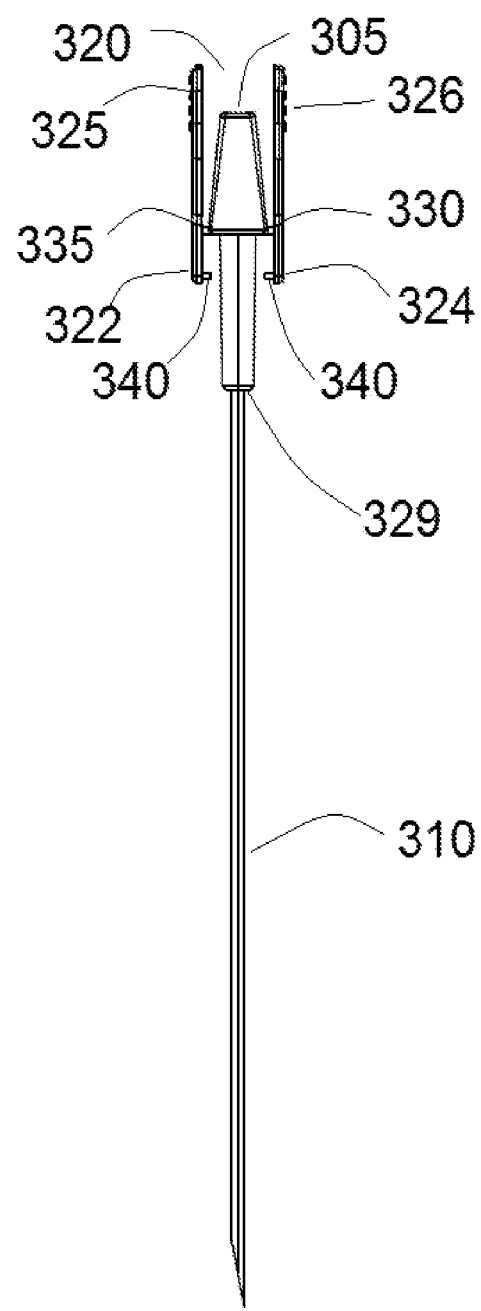
Figure 3C:
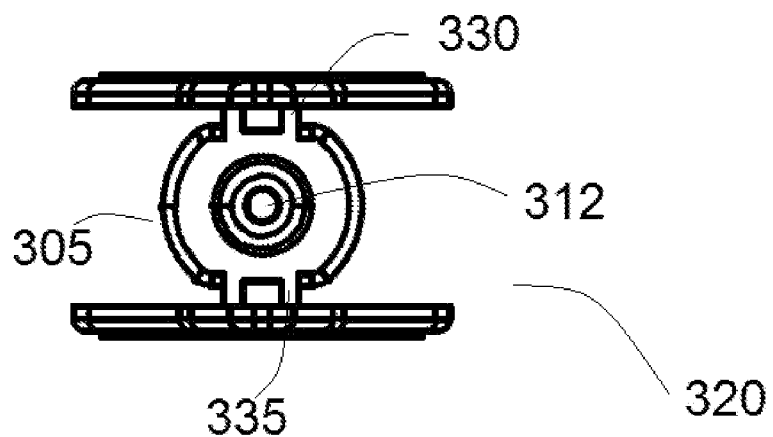

The handle 320 comprises a central portion having a lower pivot 330 and an upper pivot 335 as shown in FIGS. 3b and 3c. These pivots may be e.g. hinges, and in particular they may in some examples be spring biased hinges.

Moreover, a lower grip 326 and an upper grip 325 may be provided. The lower grip 326 is arranged to rotate around lower pivot 330, and the upper grip 325 is arranged to rotate about the upper pivot 335. Each of the distal end 324 of the lower grip 326 and the distal end 322 of the upper grip 325 includes a catch 340 which may be inserted into a recess of the catheter body (illustrated in FIG. 4). The catches 340 may be formed as fingers or protrusions extending from the distal ends of the grips.

The needle 310 may be coupled at a distal end 329 of the handle 320. In this example, the needle 310 is shown to be hollow, including a needle lumen.

The central portion of the handle 320 also comprises an opening 312, as shown in FIG. 3c, connecting with a handle lumen. In this example, the handle lumen is aligned with and continues in the lumen of the needle. A wire inserted into a proximal end 305 of the handle can thus advance into the lumen of the needle.

The removable elongated needle 310 may have diameter in the range e.g. 16 to 27 French gauge preferably 18 to 21 French gauge depending on the expected uses.

Figure 4A:
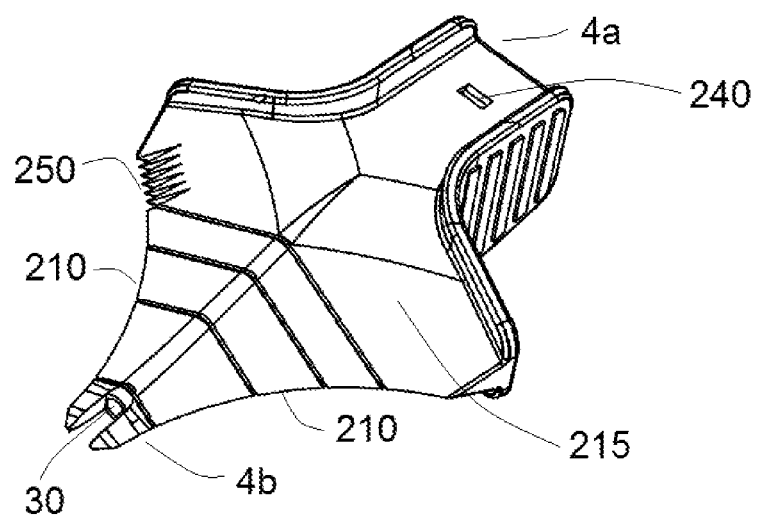
FIGS. 4a-4c schematically illustrate the example of a catheter device shown in FIGS. 2a-2c.
Figure 4B:
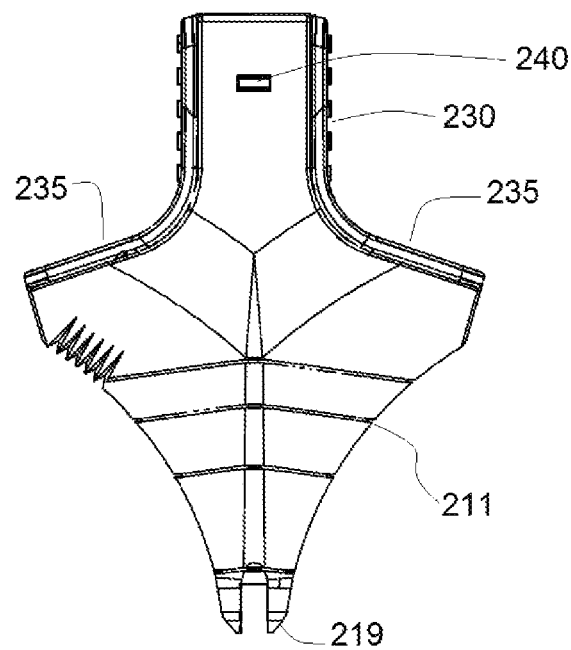
Figure 4C:
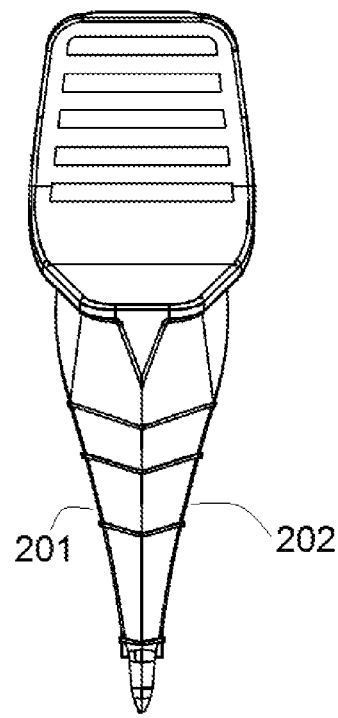

FIGS. 4a-4c schematically illustrate an example of the catheter device in more detail. The catheter body 215 may comprise an elongate channel 30 along the longitudinal length of the body extending from the proximal end 4a of the body to the distal end 4b of the body 4. A through-hole is thus formed in the body.

In some examples, the channel 30 may have the same diameter at the proximal end 4a of the body and at the distal end 4b of the body. In some other examples, the channel 30 may have a diameter at or near the proximal end 4a of the body 4 greater than that at or near the distal end 4b of the body 4 such that the diameter of the channel decreases (optionally constantly) along the longitudinal length of the body 4 extending from the proximal end 4a to the distal end 4b. This way, the channel 30 may have the shape of a funnel, thus the fastening (and the operation) of, for example, a needle device once is inserted into the channel may be improved. Particularly, the inner channel 30 may be specifically shaped to provide a seat for a needle (not shown) of a certain kind/size/shape or of a certain brand.

Front edges of the catheter body form cutting edges 210. In this particular example, the cutting edges 210 are depicted to be substantially curved. This configuration may allow a smooth initial introduction of the cutting edges 210 into the nick previously made on the patient's skin, thus the accuracy of the enlargement of the nick may be improved.

One or more of the cutting edges 210 may be provided with a saw-shaped segment 250. Particularly, this segment may be provided by a so called "crinkle" or saw tooth formation on the cutting edge of the catheter. The saw-shaped segment may comprise a series of five saw tooth formations formed in the cutting edge 210, extending along the cutting edge 210. In a modification, the number of saw tooth formation may be any suitable number depending on the material to be cut. Each formation comprises side faces. Adjacent formations may be arranged with a gap between their side faces. Such a saw shaped portion 250 may be useful for cutting a suture wire during an intervention.

In some examples, the cutting edges 210 may be protected with a cover or a protection device suitable to avoid cuts.

The most distal end of the catheter body may be made particularly sharp.

In FIGS. 4a and 4b, a recess 240 is shown in a top surface of the catheter body. This recess may mate with a catch on the handle of a needle device. Both the top surface and the bottom surface may comprise such a recess.

In this example, the top and/or bottom surface 201, 202 may further comprise one or more marks 211 indicating the extent of the incision in the skin of a patient. These marks 211 may indicate the length of the access into the patient's skin (and thus the hollow organ). Each mark may include a sign in a suitable unit of length e.g. millimeters or French. For example, the consecutive symmetric marks may be equidistantly spaced apart indicating an incision corresponding to 6 Fr, 9 Fr, 12 Fr, 15 Fr etc.

The marks may provide accurate information to the surgeon about the enlargement of the nick, thus the accuracy and the control enlarging the nick may be improved.

The catheter body may further be shaped for ergonomic handling i.e. provided with a grip 230. In particular a proximal portion may have an increased height as compared to the cutting portions. This makes it easier for a medical professional to grab and handle the catheter body. The proximal portion may further comprise a textured surface, e.g. a plurality of ribs.

In the example shown, as previously commented, the catheter body 215 may have a shape which can be considered arrow-like. The rear edges 235 as shown in FIG. 4b of the arrow may also be used for pushing forward the catheter body, e.g. to increase an original puncture.

In this example, two small sharp tips 219 are provided at the distal end of the body for facilitating the entry of the body into an initial skin nick. These two small tips are optional so that they may not be there in other examples.

Figure 5:
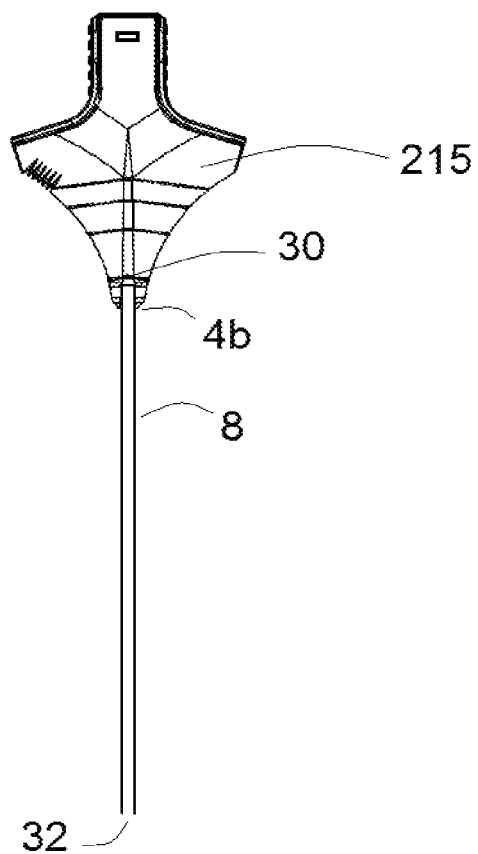
FIG. 5 schematically illustrates an example of a catheter device which is similar to the device shown in FIGS. 4a-4c but is provided with a flexible insertion tube.

FIG. 5 schematically illustrates the catheter device shown in FIGS. 4a-4c provided with a flexible insertion tube.

In this particular example, the catheter body 215 further includes a flexible insertion tube 8. The insertion tube may be made of polymers such as Teflon® or Polytetrafluoroethylene (PTFE) which is a synthetic fluoropolymer of tetrafluoroethylene. The flexible insertion tube may be coupled to the distal end 4b of the catheter body (or could alternatively be integrally formed with it).

The flexibility of the insertion tube 8 may help with a better introduction of the tube into the hollow organ. Furthermore, it can reduce the chances of the hollow organ being punctured or otherwise damaged e.g. by a sudden or accidental movement. The needle used for initial puncturing can immediately be removed, whereas a guide wire can still be introduced into the lumen of the organ through the proximal side of body and the tube.

The flexible insertion tube 8 may comprise a tubular elongate passage 32 that is aligned with the elongated channel 30 of the body 215 to define a lumen along the flexible insertion tube 8 and the catheter body.

Other aspects of the catheter device (materials, sizes, dimensions, variations etc.) could be the same as in the various embodiments illustrated before.

Figure 6A:
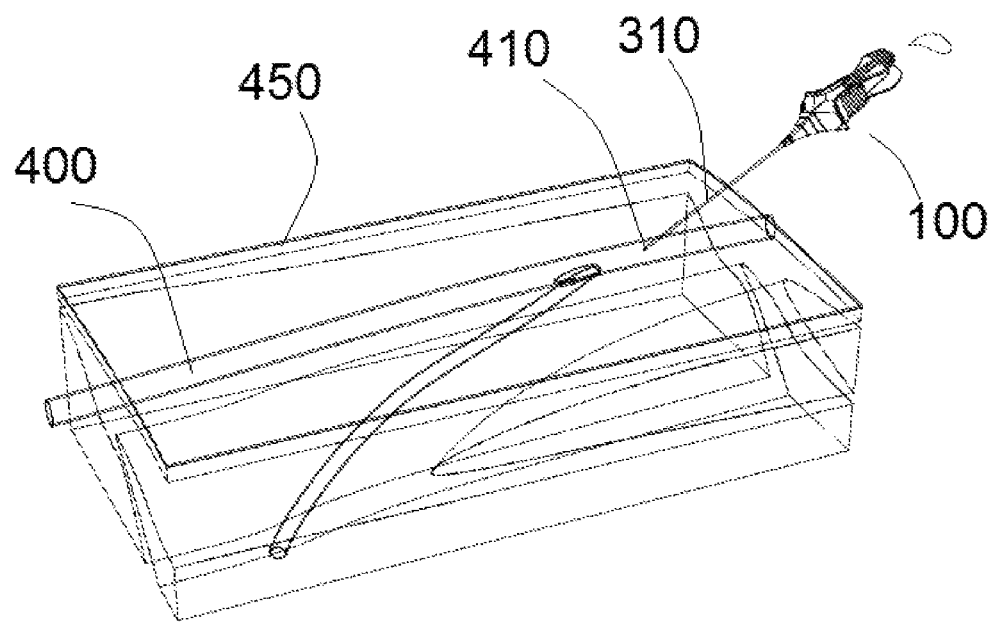
FIGS. 6a-6f schematically illustrate a sequence of situations that may occur during the performance of a method for accessing a hollow organ according to an example.

FIGS. 6a-6f schematically illustrate an example of a method of providing access to a hollow organ, which in this case is depicted to be a vein 400. An assembly 100 comprising a needle device and catheter device is provided. FIG. 6a illustrates an initial situation. The cutting end of the elongated needle 310 makes a puncture 410 in the skin 450 of a patient.

Once the removable needle reaches the vein, blood may drip out at a proximal end of the catheter, thus indicating to the user/surgeon that the needle has been properly placed into the vein.

Figure 6B:
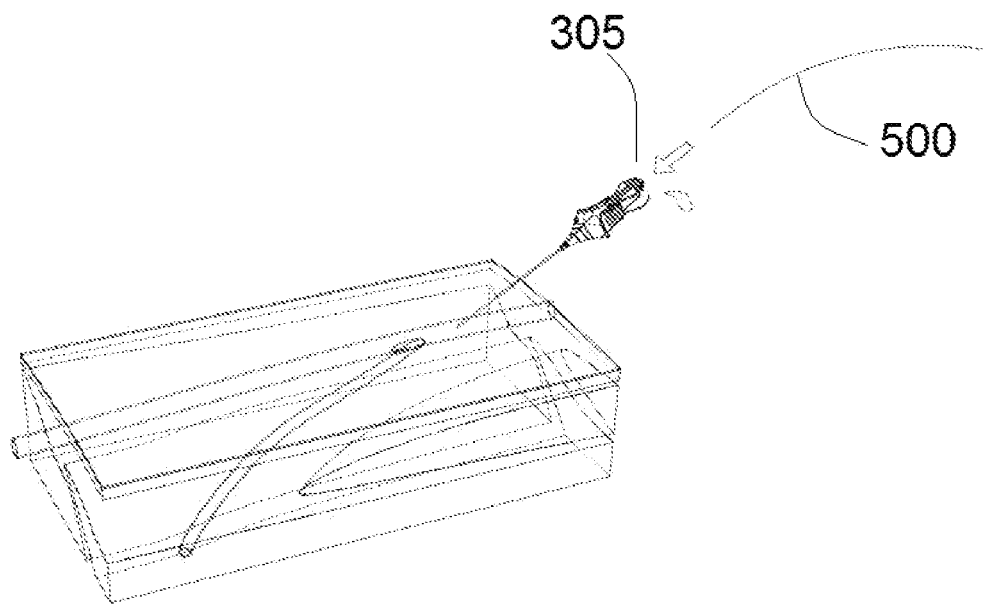

In this example, the needle is a hollow needle, and in a next step illustrated in FIG. 6b, a guide wire 500 configured to be slidably inserted and removed through a passage may be provided.

Figure 6C:
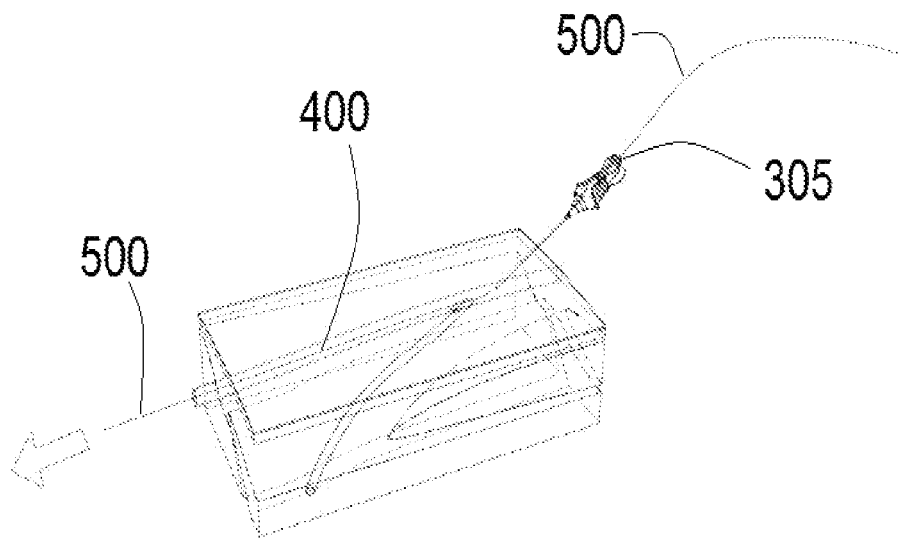

In FIG. 6c, the guide wire 500 is introduced into a proximal portion 305 of the handle of the needle device. The guide wire 500 can be advanced through the hollow needle and into the vein 400. The guide wire 500 may have a suitable diameter in order to be inserted into the lumen in the direction pointed by the arrow. The guide wire can further have a very low coefficient of friction, thus the insertion and removal may be improved. The guide wire may be made e.g. of stainless steel or nitinol, but other materials are of course possible. In some examples, the guide wire may have a handle located at or near a proximal end to facilitate control over the guide wire.

Figure 6D:
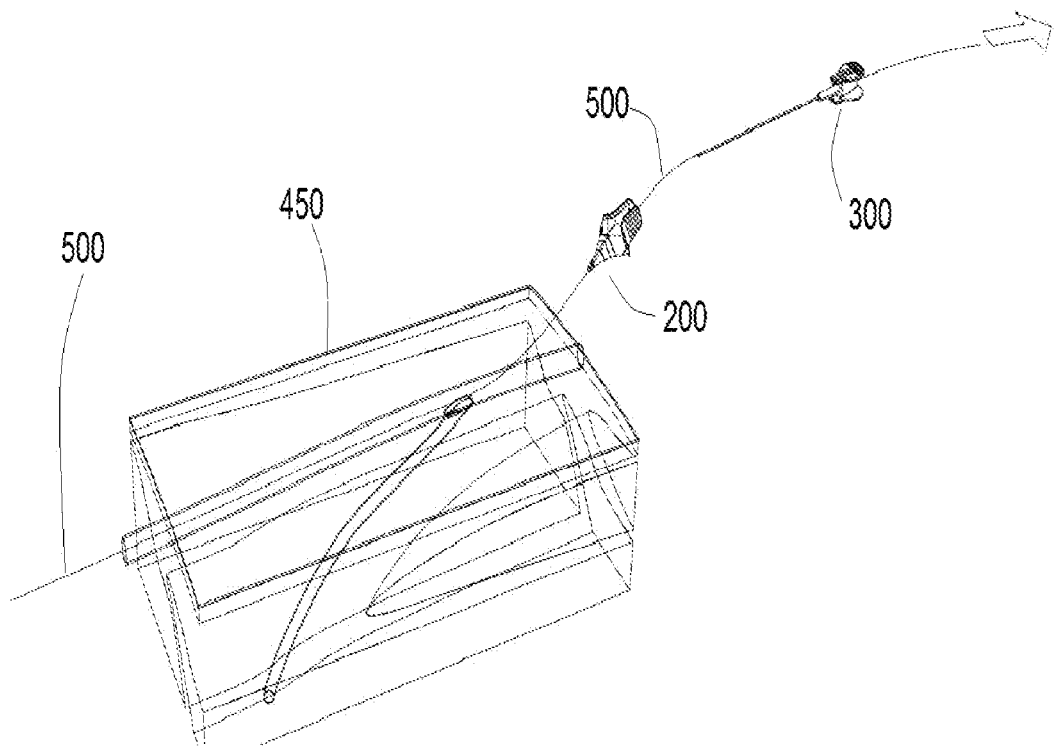

In FIG. 6d, the needle device 300 may be uncoupled from the catheter device 200. This may be done by a medical professional pushing the upper and lower grips towards each other. The catches of each of the grips may thus be released from recesses in the catheter body. The needle device can then be removed. The needle thus slides rearwardly along the central passage in the catheter body. The guide wire 500 stays in place.

Figure 6E:
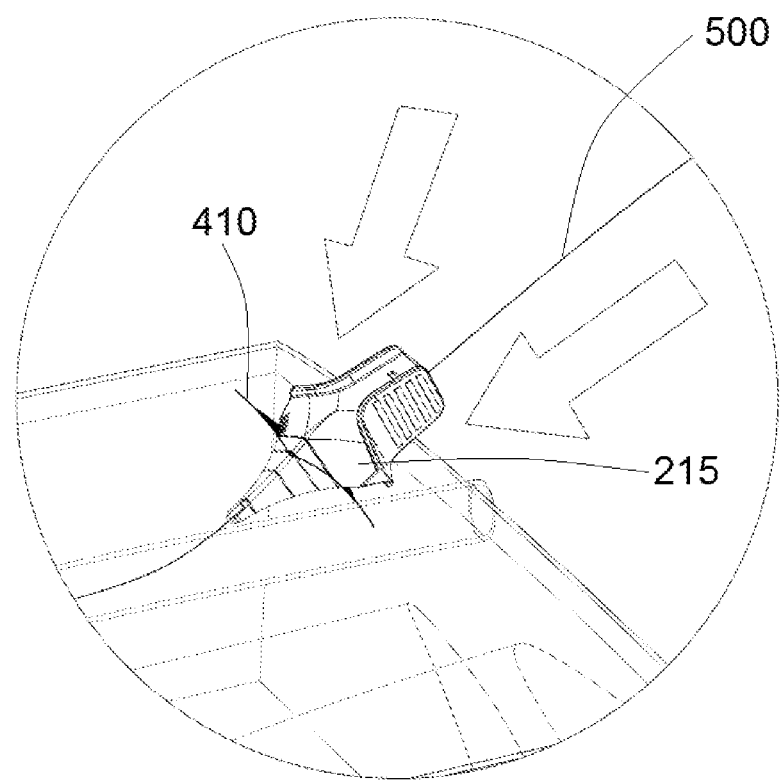

In FIG. 6e, the catheter body 215 may advance over the guide wire 500 and may be pressed by the user/surgeon towards the skin of a patient. At the same time, the skin of the patient may be tightened. The cutting edges of the catheter body may thus be introduced to increase the incision of the original puncture or nick 410 made on the skin.

Figure 6F:
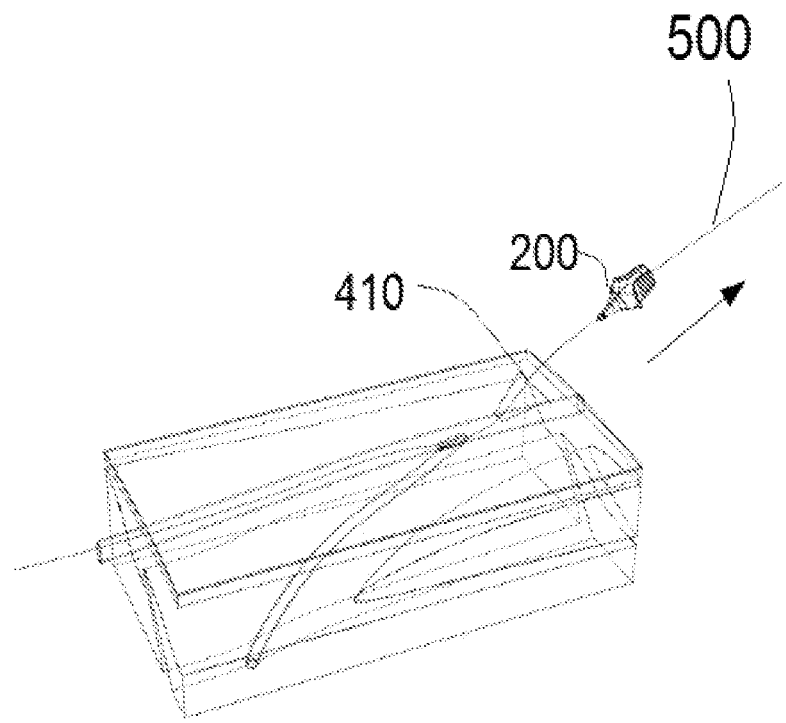

In FIG. 6f, the catheter device has already been introduced into the hollow organ (and thus the patient's skin) and the original puncture 410 of the needle has been enlarged. The catheter device 200 may thus be withdrawn. The guide wire 500 still remains located in the vein. This way, the guide wire may be used for the insertion of a treatment catheter (not shown).

A treatment catheter may comprise a conical tapered distal portion that is narrower compared to the proximal portion of the catheter. The treatment catheter may thus act as a dilator to facilitate advancement of the treatment catheter through the hollow organ. Moreover, the treatment catheter may provide additional stiffness or reinforcement in the wall of the hollow organ. Fluoroscopy may be used to confirm the position of the catheter and to maneuver it to the desired location.

Depending on the intervention, once the treatment catheter has reached its desired position, the guide wire 500 may be removed.

After completion of an intervention, the treatment catheter may be withdrawn. In some examples, a sealing device may be used to close the incision made by the procedure.

In alternative methods in which a catheter device with insertion tube is used, the main difference is that the needle device may be retracted before insertion of a guide wire. The insertion tube can be used for guiding the guide wire into the vein. After insertion of the guide wire, the method may be substantially the same as hereinbefore described.

For reasons of completeness, various aspects of the present disclosure are set out in the following numbered clauses:

Clause 1. A catheter device configured to provide access to a hollow organ comprising:
 a catheter body extending longitudinally from a proximal end to a distal end, wherein the body comprises:
  an elongate channel extending substantially along a longitudinal direction of the catheter body from the proximal end to the distal end of the catheter body, wherein the channel is configured to receive an elongated needle of a removable needle device,
  one or more cutting edges extending in a proximal direction from a distal end of the catheter body, and
  one or more recesses adapted to mate with one or more catches of the needle assembly for coupling the needle assembly to the catheter device.

Clause 2. A catheter device according to clause 1, wherein the catheter body comprises a top surface and a bottom surface, and wherein both the top surface and the bottom surface comprise a recess at or near a proximal end of the body.

Clause 3. A catheter device according to any of clauses 1-2, wherein the cutting edges are substantially straight.

Clause 4. A catheter device according to any of clauses 1-2, wherein the cutting edges are substantially curved.

Clause 5. A catheter device according to any of clauses 1-4, further comprising marks provided at one or more of the cutting edges configured to indicate the length of the access into skin of a patient.

Clause 6. A catheter device according to clause 5, wherein the marks are equidistantly spaced apart with respect to each other between 0.5 and 1.5 cm.

Clause 7. A catheter device according to any of clauses 1-6, wherein at least one of the cutting edges comprises a saw-shaped segment.

Clause 8. A catheter device according to any of clauses 1-7, further comprising a grip located at or near the proximal end of the catheter body configured to manipulate the body.

Clause 9. A catheter device according to any of clauses 1-8, wherein the catheter body is made of a polymer or mixture of polymers.

Clause 10. A catheter device according to any of clauses 1-9, further comprising a hollow insertion tube, wherein the insertion tube is attached to the catheter body at a distal end of the body, and wherein a lumen of the insertion tube is aligned with the elongated channel of the catheter body.

Clause 11. A needle device having a handle and a needle, wherein
the handle comprises a central portion incorporating a lower pivot and an upper pivot, and further comprising an upper grip arranged to rotate around the upper pivot, and a lower grip arranged to rotate around the lower pivot,
the upper grip and lower grip comprising a catch to mate with a recess in a catheter device, and
wherein the needle comprises a cutting portion at a distal end of the needle, and
wherein the central portion of the handle comprises a handle lumen.

Clause 12. A needle device according to clause 11, wherein the needle is a hollow needle having a needle lumen, and the needle lumen and the handle lumen form a continuous passage.

Clause 13. A needle device according to clause 11 or 12, wherein the catch of the upper grip is arranged at or near a distal end of the upper grip, and the catch of the lower grip is arranged at or near a distal end of the lower grip.

Clause 14. A needle device according to any of clauses 11-13, wherein the upper pivot and the lower pivot are spring biased.

Clause 15. A needle device according to any of clauses 11-14, wherein the upper grip and lower grip comprise roughness or a textured portion near a proximal end of the grips.

Clause 16. A kit including:
a catheter device according to any of clauses 1-10, and
a needle device according to any of clauses 11-15.

Clause 17. A kit according to clause 16, further comprising a treatment catheter configured to pass over a guide wire.

Clause 18. A kit according to clause 16 or 17, further comprising a guide wire configured to be advanced and removed through the channel of the catheter.

Clause 19. A method for accessing a hollow organ comprising:
providing a catheter device according to any of clauses 1-10 coupled with a needle device according to any of clauses 11-15, such that the needle of the needle device is positioned in the elongate channel of the catheter body,
making a puncture in a skin of a patient and the hollow organ using the cutting portion of the needle while in the elongate channel of the catheter device;
inserting at least a distal part of the needle into the hollow organ;
inserting a guide wire into the elongate channel of the catheter body lumen such that the guide wire is at least partially positioned in the hollow organ;
uncoupling the needle device from the catheter device;
removing the needle from the hollow organ;
increasing the length of the puncture by inserting the cutting edges of the body of the catheter device into the nick.

Clause 20. A method according to clause 19, wherein the needle is hollow, and the guide wire is inserted while the needle is still in the hollow organ.

Clause 21. A method according to clause 19, wherein the catheter device comprises an insertion tube and the guide wire is inserted after removing the needle from the hollow organ.

Clause 22. A method according to any of clauses 19-21, wherein uncoupling the needle assembly from the catheter device comprises pressing at or near a proximal end of the upper and lower grips and pivoting the upper and lower grips.

Clause 23. A method according to any of clauses 19-22, further comprising after increasing the length of the puncture, removing the catheter device over the guide wire.

Clause 24. A method according to clause 23, further comprising passing a treatment catheter over the guide wire.

Clause 25. A method according to clause 24, further comprising removing the guide wire.

Clause 26. A method according to any of clauses 19-25, wherein the length of the puncture is increased until a mark provided at the cutting edges is reached.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

What is claimed is:
1. A kit including:
a needle device comprising an elongated needle having a proximal end, a sharpened distal end and an inner lumen extending between the proximal end and the sharpened distal end;
the needle device further including a handle to which the proximal end of the elongated needle is attached, the handle including an upper grip arranged to rotate around an upper pivot and a lower grip arranged to rotate around a lower pivot, the upper grip having a proximal end portion located on a proximal side of the upper pivot and a distal end portion located on a distal side of the upper pivot, the lower grip having a proximal end portion located on a proximal side of the lower pivot and a distal end portion located on a distal side of the lower pivot, the upper grip including a first inwardly protruding catch, the lower grip including a second inwardly protruding catch; and a catheter device configured to provide access to a hollow organ, the catheter device configured to be used with the needle device and comprising a catheter body, the catheter body comprising:
  a proximal end, a distal end, and an outer surface;
  a grip located at or near the proximal end of the catheter body, the grip being configured to allow manipulation of the catheter body by a user of the catheter device;
  an elongate internal channel extending between the proximal end of the catheter body and the distal end of the catheter body, the elongate internal channel being configured to receive the elongated needle;
  one or more cutting edges extending in a proximal direction from a location at or near the distal end of the catheter body, the one or more cutting edges and the catheter body being monolithically formed; and
  a first recess and a second recess in the outer surface, each of the first recess and the second recess being located in a proximal end portion of the catheter body, an inside of the first recess and of the second recess being configured to respectively receive the first inwardly protruding catch and the second inwardly protruding catch of the needle device for detachably coupling the needle device to the outer surfaces of the catheter body.

2. The kit according to claim 1, further comprising a treatment catheter configured to pass over a guide wire.

3. The kit according to claim 2, wherein the guide wire is configured to be advanced and removed through the elongate internal channel of the catheter device.

4. The kit according to claim 1, wherein the outer surface of the catheter body includes a top surface and a bottom surface, and wherein the first recess is located in the top surface and the second recess is located in the bottom surface.

5. The kit according to claim 4, wherein the grip includes a first side surface and a second side surface facing in opposite directions and separated by a first distance, at least a proximal portion of each of the top surface and the bottom surface of the catheter body having a width that extends entirely across the first distance.

6. The kit according to claim 5, wherein the first recess and the second recess are located between the first side surface and the second side surface of the grip.

7. The kit according to claim 1, wherein the catheter device further comprises a flexible insertion tube.

8. The kit according to claim 1, wherein the one or more cutting edges of the catheter device are straight.

9. The kit according to claim 1, wherein the one or more cutting edges of the catheter device are curved.

10. The kit according to claim 1, wherein the catheter body is made of a polymer or a mixture of polymers.

11. The kit according to claim 1, wherein the catheter body includes one or more marks at one or more of the one or more cutting edges, the one or more marks being configured to indicate a length of a cut into skin of a patient.

12. A method for accessing a hollow organ comprising:
  providing a needle device and a catheter device,
    the needle device comprising an elongated needle having a proximal end, a sharpened distal end and an inner lumen extending between the proximal end and the sharpened distal end; the needle device further including a handle to which the proximal end of the elongated needle is attached, the handle including an upper grip arranged to rotate around an upper pivot and a lower grip arranged to rotate around a lower pivot, the upper grip having a proximal end portion located on a proximal side of the upper pivot and a distal end portion located on a distal side of the upper pivot, the lower grip having a proximal end portion located on a proximal side of the lower pivot and a distal end portion located on a distal side of the lower pivot, the upper grip including a first inwardly protruding catch, the lower grip including a second inwardly protruding catch,
    the catheter device being configured to provide access to the hollow organ, the catheter device including a catheter body, the catheter body having:
      a proximal end, a distal end, and an outer surface;
      a grip located at or near the proximal end of the catheter body, the grip being configured to allow manipulation of the catheter body by a user of the catheter device;
      an elongate internal channel extending between the proximal end of the catheter body and the distal end of the catheter body, the elongated needle residing inside the elongate internal channel;
      one or more cutting edges extending in a proximal direction from a location at or near the distal end of the catheter body, the one or more cutting edges and the catheter body being monolithically formed;
      a first recess and a second recess in the outer surface, each of the first recess and the second recess being located in a proximal end portion of the catheter body, an inside of the first recess and of the second recess being configured to respectively receive the first inwardly protruding catch and the second inwardly protruding catch of the needle device for detachably coupling the needle device to the outer surface of the catheter body;
  making a puncture in skin of a patient and the hollow organ using the sharpened distal end of the elongated needle while in the elongate internal channel of the catheter device;
  inserting at least a distal part of the elongated needle into the hollow organ;
  inserting a guide wire into the elongate internal channel of the catheter body such that the guide wire is at least partially positioned in the hollow organ;
  detaching the needle device from the catheter device by respectively removing the first inwardly protruding catch and the second inwardly protruding catch of the needle device from the first recess and the second recess of the catheter body;
  removing the elongated needle from the hollow organ; and subsequently
  increasing a length of the puncture by inserting the one or more cutting edges of the catheter body of the catheter device into the puncture by guiding the catheter body directly over the guide wire.

13. The method according to claim 12, wherein the guide wire is inserted while the elongated needle is in the hollow organ.

14. The method according to claim 12, wherein the catheter device comprises an insertion tube and the guide wire is inserted after removing the elongated needle from the hollow organ.

15. The method according to claim 14, wherein the insertion tube remains in the hollow organ at least until the guide wire is inserted into the hollow organ.

16. The method according to claim 12, further comprising after increasing the length of the puncture, removing the catheter device from the puncture over the guide wire.

17. The method according to claim 16, further comprising passing a treatment catheter over the guide wire.

18. The method according to claim 12, wherein detaching the needle device from the catheter device comprises pressing at or near a proximal end of the upper grip and the lower grips and pivoting the upper grip and the lower grip.

19. The method according to claim 12, wherein the catheter body includes one or more marks at one or more of the one or more cutting edges, and wherein the length of the puncture is increased by inserting the one or more cutting edges of the catheter body of the catheter device into the puncture until one of the one or more marks reaches the skin.

20. The method according to claim 12, wherein the catheter body is made of a polymer or mixture of polymers.

* * * * *